United States Patent
Lacombe et al.

(10) Patent No.: US 7,911,590 B2
(45) Date of Patent: Mar. 22, 2011

(54) METHOD AND SYSTEM FOR MEASURING THE SPEED OF BLOOD FLOW

(75) Inventors: Francois Lacombe, Chaville (FR); Georges Le Goualher, La Meziere (FR); Aymeric Perchant, Fontenay Sous Bois (FR); Nicholas Ayache, Nice (FR)

(73) Assignee: Mauna Kea Technologies, Paris (FR)

( * ) Notice: Subject to any disclaimer, the term of this patent is extended or adjusted under 35 U.S.C. 154(b) by 1114 days.

(21) Appl. No.: 11/547,197

(22) PCT Filed: Mar. 25, 2005

(86) PCT No.: PCT/FR2005/000718
§ 371 (c)(1), (2), (4) Date: Sep. 29, 2006

(87) PCT Pub. No.: WO2005/098474
PCT Pub. Date: Oct. 20, 2005

(65) Prior Publication Data
US 2008/0045848 A1     Feb. 21, 2008

(30) Foreign Application Priority Data
Apr. 2, 2004   (FR) .................................... 04 03519

(51) Int. Cl.
*G01P 3/36* (2006.01)
(52) U.S. Cl. ........................................................ 356/28
(58) Field of Classification Search ............ 356/28, 356/3.01–3.15, 4.01–4.1, 5.01–5.15, 6–22, 356/28.5
See application file for complete search history.

(56) References Cited

U.S. PATENT DOCUMENTS

| 5,333,044 | A  | * | 7/1994 | Shaffer ........................... 356/28 |
| 6,540,981 | B2 | * | 4/2003 | Klaveness et al. ............ 424/9.6 |
| 2005/0242298 | A1 | | 11/2005 | Genet et al. |
| 2006/0003881 | A1 | * | 1/2006 | Houwen ........................ 494/37 |
| 2006/0132790 | A1 | * | 6/2006 | Gutin ............................. 356/479 |

FOREIGN PATENT DOCUMENTS

WO    2004/051310    6/2004

OTHER PUBLICATIONS

Wayland et al., "Erythrocyte velocity measurement in microvessels by a two-slit photometric method," *Journal of Applied Physiology*, vol. 22, No. 2, 1967, pp. 333-337.

(Continued)

*Primary Examiner* — Thomas H Tarcza
*Assistant Examiner* — Like D Ratcliffe
(74) *Attorney, Agent, or Firm* — Young & Thompson

(57) ABSTRACT

The invention relates to a method for measuring the speed of a particle such as a red blood cell moving inside a flow such as a flow of the blood, using a light scanning microscope. The inventive method comprises the following steps: acquisition of an image by x and y light scanning on a plane containing the object; detection on the plane (x, y) of a mark on the plane (x, y); estimation of the speed $v_g$ of the object from the gradient thus determined.

21 Claims, 2 Drawing Sheets

OTHER PUBLICATIONS

Groner et al., "Orthogonal polarization spectral imaging: A new method for study of the microcirculation," *Nature Medicine*, vol. 5, No. 10, Oct. 1999, pp. 1209-1213. Sato et al., "Measuring microcirculation using spatiotemporal image analysis," *Lecture Notes in Computer Science*, vol. 905, 1995, pp. 302-308.

Kleinfeld et al., "Two-photon imaging of cortical microcirculation," *Imaging in Neuroscience and Development*, Yuste and Konnerth (editors), CSHL Press, 9 pp., Oct. 28 2003.

Chaigneau et al., "Two-photon imaging of capillary blood flow in olfactory bulb glomeruli," *PNAS*, Oct. 28, 2003, vol. 100, No. 22, pp. 13081-13086.

* cited by examiner

METHOD AND SYSTEM FOR MEASURING THE SPEED OF BLOOD FLOW

This invention relates to a method for measuring the velocity of a microscopic object moving inside a flow, such as a blood flow, using a light-scanning microscope.

It applies in particular but not exclusively to the study of microcirculation in which the difficulty is detecting particles such as moving red blood cells or leucocytes, estimating the direction of movement of these particles as well as their velocities.

This invention can however apply to other fields such as for example microfluidics.

Estimation of the velocity of movement of an object using an imaging system conventionally occurs using a sequence of images representing this object in movement. The basic hypothesis being that the acquisition rate of the imaging system is such that the object makes small movements from one image to the next. The presence of the object, at different positions, on the image time series then makes it possible to ascertain the velocity of the latter by means of a calibration of the acquisition system.

The document "Erythrocyte velocity measurement in microvessels by a two-slit photometric method," by H. Wayland and R. C. Johnson, published in J. Appl. Physiol. 22(2): 333-337, 1967, describes a two-slit photometric method. The two-slit photometric measurement method is probably the oldest known technique for automatically measuring the velocity of blood flow. This method measures the velocity of red blood cells and preferably applies to the capillaries and small venules in which blood cells circulate in single file, isolated or in small aggregates. The measurement is carried out on a video sequence, using two slits placed on the screen showing the sequence. The two slits are parallel and perpendicular to the vessel on which the measurement is carried out. A photodiode is present opposite each of the two slits. The apparatus used proposes two measurement methods. In a first method, the two slits are spaced apart (at an equivalent distance on the tissue) from 45 µm to 70 µm. The measurement of velocity is carried out by calculation of the intercorrelation of the two signals originating from the photodiodes. In the second measurement method, the two slits are very close together: 7.4 µm equivalent tissue distance, i.e., a distance slightly less than the mean diameter of a red blood cell. Consequently, two consecutive signals generated by the upstream diode and the downstream diode respectively are caused by the same blood cell, and it is therefore possible to calculate the velocity of this blood cell. However, the limitations of the method are the need to carry out the measurement on very fine vessels in order to limit the observation to one red blood cell, and the velocities measured which, as a result of the image frequency of 30 images per second, cannot exceed 2 mm/s.

The spatiotemporal projection method ("Line shift diagram") is also known. This method is an extension of the preceding one. Instead of sampling the signal at two points, the user selects a zone of interest, i.e. a rectangle marked in a vessel. In each image, a mean of the grey scale is calculated over the width of the vessel at each point of the axis of the vessel, the signal of the zone of interest is projected in one dimension on the axis of the vessel. Then the unidimensional signals obtained for each image are aligned vertically in order to produce a spatiotemporal image which shows the traces of the blood cells. The velocity is evaluated by correlating the adjacent signals. This method is used by the CapImage® and Capiscope® software programs, together with the Cytoscan® acquisition apparatus. Such a method is in particular described in the document "Orthogonal Polarization Spectral Imagina: A new method for study of microcirculation." by W. Groner, I. W. Winkelman, A. G. Harris, G. Inde, G. I. Bouma, K. Messmer, and R. G. Nadeau, published in Nature Medicine, 5: 1209-1213, 1999. The main limitation is the velocity range measured, which cannot exceed 2 mm/s because of the image frequency (25 images/second or 50 images/second if the measurements are alternatively carried out on the two interlaced fields of the video flow).

The SLO (scanning laser ophthalmoscope), is an apparatus the principle of which is based on non-fibre confocal microscopy. The images are captured at a rate of 50 interlaced images per second. The velocity measurement method used by this apparatus is based on cell monitoring. The same image is constituted by interlaced fields corresponding to two instants separated by 20 ms, a moving blood cell therefore appears at two different places on the image, once on the even lines and again on the odd lines. Once the two images of the blood cell are located, measurement of the velocity is immediate. The wide field of the apparatus (up to 1200 µm) makes it possible to measure velocities of several cm/s. The limitations of this apparatus are mainly due to the monitoring of the blood cells: marked blood cells of a large size (12 µm for the leucocytes) and in a small number are required. Such a method seems not to be applicable to the measurement of the velocity of red blood cells the dimensions of which are smaller (7-8 µm), at a much greater concentration (1,000 times greater than that of the leucocytes) and more difficult to label.

Another measurement method which is commonly coupled with Cytoscan® or SLO is the measurement of red blood cell velocity by the Doppler effect. The Doppler effect describes the frequency shift experienced by a wave reflected by an object which is moving relative to the observer. In the case of blood flow, the moving objects are the red blood cells. A single frequency wave (for example a laser) of a given wavelength is sent along a blood vessel. Measurement of the velocity by Doppler effect has the advantage of being very rapid and precise. Depending on the material and the analysis software used the maximum measurable velocities vary from 1 mm/s to several cm/s. A drawback of the Doppler effect is the difficulty with precisely identifying the zone in which the velocity is measured, especially in depth. The light reflected can originate from different vessels where the blood circulates at different velocities.

The spatiotemporal analysis method is also known. Such a method for measurement of the velocity of leucocytes is described in the document "Measuring microcirculation using spatiotemporal image analysis." by Yoshinobu Sato et al., CVRMed, pages 302-308, 1995. This analysis comprises three main stages: i) Firstly, the vessel is extracted from the image by a segmentation carried out on the histogram of the temporal variances of the pixels of the frames of the sequence. ii) A spatiotemporal image is then constructed from the successive images of the vessel. This image can be three-dimensional, or two-dimensional if each image of the sequence is projected along the axis or the contours of the vessel. iii) The traces left in the spatiotemporal image by the movement of the leucocytes are then reinforced by application of a filter bank with selective orientation (for example a Gabor filter bank) The traces are extracted by thresholding the best responses. The last stage involves connecting the traces together in order to reconstitute the entire trajectories of the leucocytes. Obtaining these traces then makes it possible, by calculation of their tangents, to arrive at an estimation of the velocity of the leucocytes over their trajectories.

Also known in the field of spatiotemporal analysis are the documents:

"*Two-photon imaging of neocortical microcirculation.*" D. Kleinfeld and W. Denk; In Imaging Neurons: A Laboratory Manual (R. Yuste, F. Lanni, and A. Konnerth, editors), 1999, Cold Spring Harbor Laboratory Press, NY, pp. 23.1-23.15; accessible on the Internet at the following address:
http://physics.ucsd.edu/neurophysics/publications/kleinfeld_de nk_cshl_2003.pdf; and "*Two-photon imaging of capillary blood flow in olfactory bulb glomeruli*" E. Chaigneau et al., PNAS, 28 Oct. 2003; 100 (22): 13081-13086; accessible on the Internet at the following address:
http://www.pnas.org/cgi/content/full/100/22/13081.

These documents describe a method for measuring velocity by carrying out, using a non-fibre microscope, several successive scannings along the axis of the blood vessel. Several "unidimensional" images are thus obtained from the same segment at different successive instants. These images are placed end-to-end so as to form an overall visualization the ordinate of which is a time reference. The movement of the particles in the blood vessel is shown in the form of oblique bands. The spot velocity is determined by calculating the slope-of each band on the overall visualization. However, the drawback of this method lies in the fact that it is essential to position the acquisition apparatus parallel to the axis of the blood vessel. Moreover, in order to constitute the overall visualization the acquisition of several images from the same segment is necessary.

In most of the techniques which have just been presented, the velocity measurement is based on an analysis of at least two successive images of an acquisition; which in addition creates problems of blurring and of making the images correspond. Consequently, the velocity range which can be measured by these techniques depends on the field of view as well as the image frequency. For scanning imaging systems having a small field of view, for example of the order of 166 µm×118 µm, and rates of acquisition, for example of the order of 12 images per second, a particle moving at a velocity greater than 1.8 mm/s will pass through the field of observation between two successive images, which makes it impossible to use most of the techniques mentioned previously.

This invention aims to overcome the above-mentioned drawbacks by proposing a method which is able to measure the velocity of the red blood cells in particular.

The object of the present invention is to measure the velocity of particles in rapid movement by means of a scanning imaging system. By rapid movement is meant a velocity greater than approximately 2 mm/s.

The desired object is achieved with a method for measuring the velocity of a microscopic object, such as for example red blood cells and leucocytes moving inside a flow, such as a blood flow, using a light-scanning microscope. According to the invention, this method comprises the following steps:

acquisition of an image by light scanning in the x and y directions of a plane containing said object, this plane is also called a subsurface image field situated at a few µm into a sample or a biological tissue;

detection in the plane (x, y) of a ridge produced by the movement of said object during the acquisition of said image;

determination of the slope of said ridge in the plane (x, y);

estimation of the velocity $V_g$ of said object from the thus-determined slope.

It is possible to use a confocal or non-confocal light scanning microscope, in particular laser scanning, in a fibre or non-fibre mode. In order to implement the non-fibre embodiment it is possible to use, by adapting the processing electronics, an apparatus of the SLO type or any other (x, y) scanning image acquisition apparatus, the scanning velocities of which are suited to the implementation of the method according to the invention.

In addition to the above, it is possible to use, in a non-limitative manner, a fibre, in particular a monofibre, laser, confocal or non confocal microscope, with distal scanning. This distal scanning can be realized by a micromirror, by movement of lenses or optics, by spectral scanning. It is also possible to use a monofibre system with proximal scanning where the light scanning is obtained by deviation of one end of the optical fibre within an optical head close to the observed object.

In contrast to the spatiotemporal analysis methods of Kleinfeld and Chaigneau where a succession of "unidimensional" images is acquired from the same segment in the axis of the blood vessel, in the present invention it is possible to use a single image acquired by a two-dimensional plane scanning.

In contrast to the prior art where the ridges are measured on a spatiotemporal image (t=f(x)), here the ridges are completely different since they come from a plane image (y=f(x)), the temporal concept being induced in the point by point scanning system in the "Z" direction. Advantageously a morphological image is used. For example, in Yoshinobu Sato's document of the prior art, in order to obtain ridges, several images are produced in which a single line is extracted from each image, and thus the final image t=f(x) is developed.

The use of a scanning imaging system, a system in which the moving object will be observed during the generation time of an image (frame crossing time), leads to the appearance of ridges making it possible to arrive at an estimation of the velocity of moving objects from a single image. These ridges therefore originate from the interaction between the moving object and the scanning system. The invention is in particular remarkable because these ridges are generally considered by a person skilled in the art as interference to be eliminated from a scanning imaging system. Use is therefore made of the elements considered to be aberrations in laser scanning microscopes, in particular in fibre mode. For this purpose, the invention comprises a step of detection of ridges in which the following steps are carried out:

enhancement of a group of ridges of the image by application of a filter;

application of a threshold in order to retain the most significant ridges;

fitting a straight line or an ellipse on each of these ridges; and identification of said ridge.

According to the invention, given the orders of magnitude of the scanning velocities and those of the objects observed, it is possible to simplify the model of the trajectory of the light-spot. A first simplification involves considering the trajectory of the spot as horizontal on the acquisition window. This simplification is justified by the ratio of one thousand existing between the horizontal velocity and the vertical velocity of the spot, the calculation confirms that the vertical position of the spot varies by less than 0.1 µm on the acquisition window.

A second approximation is to consider the time necessary for the spot to horizontally cover the acquisition window as negligible, i.e., considering the objects as immobile during the path of a scanning line. The velocity of the objects observed (in the vessels considered, the red blood cells have a velocity of less than 20 mm/sec) relative to the horizontal velocity of the spot (>1 m/s) justifies this approximation.

Finally the scanning is modelled with instantaneous horizontal scanning lines spatially separated by a distance $V_y/f_x$, with $f_x$ being the frequency of the "x" scanning.

Once the scanning has been modelled, the moving objects, for example the red blood cells, then have to be modelled. Several models have been envisaged in order to describe the red blood cells: from the simple rod to a realistic three-dimensional model.

The simplest model which is able to take account of the deformations observed involves a red blood cell being represented by a vertical rod. In the case of use of this model, a simple equation is obtained linking the angle a of the ridges observed (relative to the "x" axis) with the vertical velocity of the scanning $V_y$ and with the velocity of horizontal movement $V_g\cos(\theta)$ of the blood cell:

$$\tan\alpha = \frac{V_y}{V_g\cos\theta} \qquad (1)$$

with $V_y$ being the vertical velocity of the light spot used for the scanning, $V_g$ the velocity of the sought blood cell, $\theta$ the angle between the vector $V_g$ and the x axis of rapid scanning. Tan($\alpha$) is the slope of the ridges.

If the trajectory of the blood cells is considered to be colinear with the edges of the vessel carrying the object then it is possible to work out $\theta$ by detecting the edges of the vessel and thus to arrive at the velocity $V_g$ of the blood cell.

In the general case where $\theta$ is not known but where the length L of the ridge is known, two possibilities can be envisaged:

1) The size D of the blood cell is known.

In this case, $t_v$ is considered to be the visibility time of the blood cell, defined as the time which passes between the first intersection and the last intersection of the trajectories. The blood cell has a vertical velocity $V_g\sin(\theta)$ and a vertical spread D. The object is therefore compared to a bar perpendicular to the direction of flow, with a sufficiently large finished length to spread over several horizontal scanning lines. The spot is punctiform and has a vertical velocity $V_y$, $t_v$ therefore depends only on the difference in vertical velocity of the spot and the blood cell, and of D according to the equation:

$$t_v = \frac{D}{|V_y - V_g\sin\theta|} \qquad (2)$$

The vertical $L|\sin((\alpha)|$ and horizontal $L|\cos(\alpha)|$ spreads of the ridge observed are directly connected to $t_v$ and to the vertical velocity of the spot and the horizontal velocity of the blood cell by:

$$L|\sin\alpha|=t_v|V_y|$$

$$L|\cos\alpha|=t_vV_g|\cos\theta| \qquad (3)$$

Equations 2 and 3 allow the following to be stated:

$$L = \frac{D}{|V_y - V_g\sin\theta|}\sqrt{V_y^2 + V_g^2\cos^2\theta} \qquad (4)$$

Which, combined with the equation (1), produces a system of two equations with two unknowns $\theta$ and $V_y$. The resolution must take place according to the sign of $V_y-V_g\sin(\theta)$, i.e. according to whether the spot moves vertically more or less quickly than the blood cell.

In the case where the two velocities are equal, the visibility time becomes infinite and the ridge becomes infinitely long. We then have $V_g\sin(\theta)=V_y$, and by replacing in the equation (1), this implies that $\tan(\alpha)=\tan(\theta)$. Consequently, the ridge is exactly the trajectory of the blood cell and the velocity $V_g$ is given by:

$$V_g = \left|\frac{V_y}{\sin\alpha}\right| \qquad (5)$$

If the light spot moves vertically more quickly than the blood cell ($V_y>V_g\sin(\theta)$), then the resolution of system (3) gives:

$$\tan\theta = \tan\alpha - \frac{D}{L\cos\alpha} \qquad (6)$$

$$V_g = |V_y|\sqrt{\left(1 - \frac{D}{L\sin\alpha}\right)^2 + \frac{1}{\tan^2\alpha}}$$

If the light spot moves vertically less quickly than the blood cell ($V_y<V_g\sin(\theta)$), then the resolution of system (3) gives:

$$\tan\theta = \tan\alpha + \frac{D}{L\cos\alpha} \qquad (7)$$

$$V_g = |V_y|\sqrt{\left(1 + \frac{D}{L\sin\alpha}\right)^2 + \frac{1}{\tan^2\alpha}}$$

2) When a reversed scanning is available:

If there is another scanning available, which is reversed relative to the previous one, i.e. with a vertical velocity $-V_y$, a ridge with an angle $-\alpha$ and with a length L' will be observed. L' is given by:

$$L' = \frac{D}{|-V_y - V_g\sin\theta|}\sqrt{V_y^2 + V_g^2\cos^2\theta} \qquad (8)$$

The ratio between the equations (4) and (8) allows the following to be stated:

$$\frac{L}{L'} = \frac{|V_y + V_g\sin\theta|}{|V_y - V_g\sin\theta|} \qquad (9)$$

two cases must then be distinguished: $|V_y|>|V_g\sin(\theta)|$ and $|V_y|<|V_g\sin(\theta)|$ (if $|V_y|=|V_g\sin(\theta)|$, then the equation (5) applies).

If $|V_y|>|V_g(\sin(\theta)|$ then the resolution gives:

$$\tan\theta = \tan\alpha\frac{L - L'}{L + L'} \qquad (10)$$

$$V_g = |V_y|\sqrt{\left(\frac{L-L'}{L+L'}\right)^2 + \frac{1}{\tan^2\alpha}}$$

If $|V_y| < |V_g \sin(\theta)|$ then the resolution gives:

$$\tan\theta = \tan\alpha \frac{L+L'}{L-L'} \quad (11)$$

$$V_g = |V_y|\sqrt{\left(\frac{L+L'}{L-L'}\right)^2 + \frac{1}{\tan^2\alpha}}$$

In all of the above, the object, such as a red blood cell, is compared to a vertical rod with a length D. A person skilled in the art will easily understand that it is possible to replace this hypothesis with the more realistic one of a sphere (or disc), or an ellipse or an even more complicated structure and to evaluate the difference between the state observed in this case and that observed in the simple case. Whether or not this difference should be taken into account will depend on the precision sought.

By way of example, the red blood cell can be represented in the form of a solid sphere or a biconcave shape possessing a rotational symmetry. In both cases, the orthogonal projection in the observation plane is compared to a disc with a radius R. In the acquired image, this moving disc appears as an ellipse the angle α of which between the ridge and the "x" axis is given by:

$$\tan(2\alpha) = \frac{2\cos(\theta)}{\frac{V_g}{V_y} - 2\sin(\theta)} \quad (12)$$

The length of the principal axis is given by:

$$L = \frac{2R\sqrt{2}}{\sqrt{V_r^2 - 2V_r\sin(\theta) + 2 - |V_r|\sqrt{V_r^2 - 4V_r\sin(\theta) + 4}}} \quad (13)$$

with $V_r = \frac{V_g}{V_y}$ and R the radius of the disc considered.

Digital simulations carried out with more complex models or representing the red blood cells (toroidal surfaces) show that the disc model is sufficient to represent the red blood cells.

If the orientation θ of the trajectory of the blood cell is unknown, but the length L of the ridges is available, it is possible to partially calculate velocity information. Equations (12) and (13) form a system linking the pair (α, L) which are the parameters which can be observed during the acquisitions to the pair (θ, $V_g$) which are the sought parameters.

According to another feature of the invention, a confocal microscopy system with light scanning in fibre mode is proposed, used to measure the velocity of the microscopic object moving inside a flow, such as a blood flow, this system comprising:

means for acquiring an image by x and y light scanning of a plane containing said object;
means for detecting a ridge produced by the movement of said object during the acquisition of said image;
means for determining the slope of said ridge; and
means for estimating the velocity $V_g$ of said object from the thus-determined slope.

Other advantages and characteristics of the invention will become apparent on examining the detailed description of an embodiment which is in no way limitative and the attached drawings where:

Although the invention is not limited to this, the method according to the invention implemented in a confocal microscope with laser scanning in fibre mode will now be described, this method applying to the field of microcirculation, the orders of magnitude of which are as follows:

the arterioles have a diameter which varies between 50 μm and 100 μm; the capillaries are much finer with a diameter of 3 μm to 8 μm; finally the venules have a diameter of 30 μm to 50 μm;

the velocity of the red blood cells in these vessels is comprised within a range from less than 1 mm/s for the smallest vessels to several tens of mm/s for the arterioles;

the red blood cells are cells the mean diameter of which is approximately 7 μm, compared with diameters of 10 μm to 15 μm for the leucocytes.

In a general manner, in order to implement the present invention, the system described in the document WO 2004/008952A1, "Method and equipment for fibre optic high-resolution, in particular confocal, fluorescence imaging", Mauna Kea Technologies, may be used as a basis, in which document an image guide is used consisting of several thousands of optical fibres, an excitation signal being emitted by a source, deflected and injected by turns into one of the fibres of said guide, each excitation point of the tissue at the fibre outlet emitting in return a fluorescence signal collected by said fibre, then detected and digitized to form an image element. According to a first aspect, the method described in this document WO2004/008952A1 provides for the focussing of the beam in the fibre outlet to excite a subsurface plane and produce a confocal image. According to a second aspect, the method provides for the production of a divergent beam in the fibre output capable of exciting a microvolume of the tissue from the surface. The excitation signal is deflected at a velocity corresponding to acquisition of a number of images per second sufficient for real time use and the fluorescence signal is detected at a detecting frequency corresponding to a minimum frequency for sampling the fibres one by one.

Figure 1:
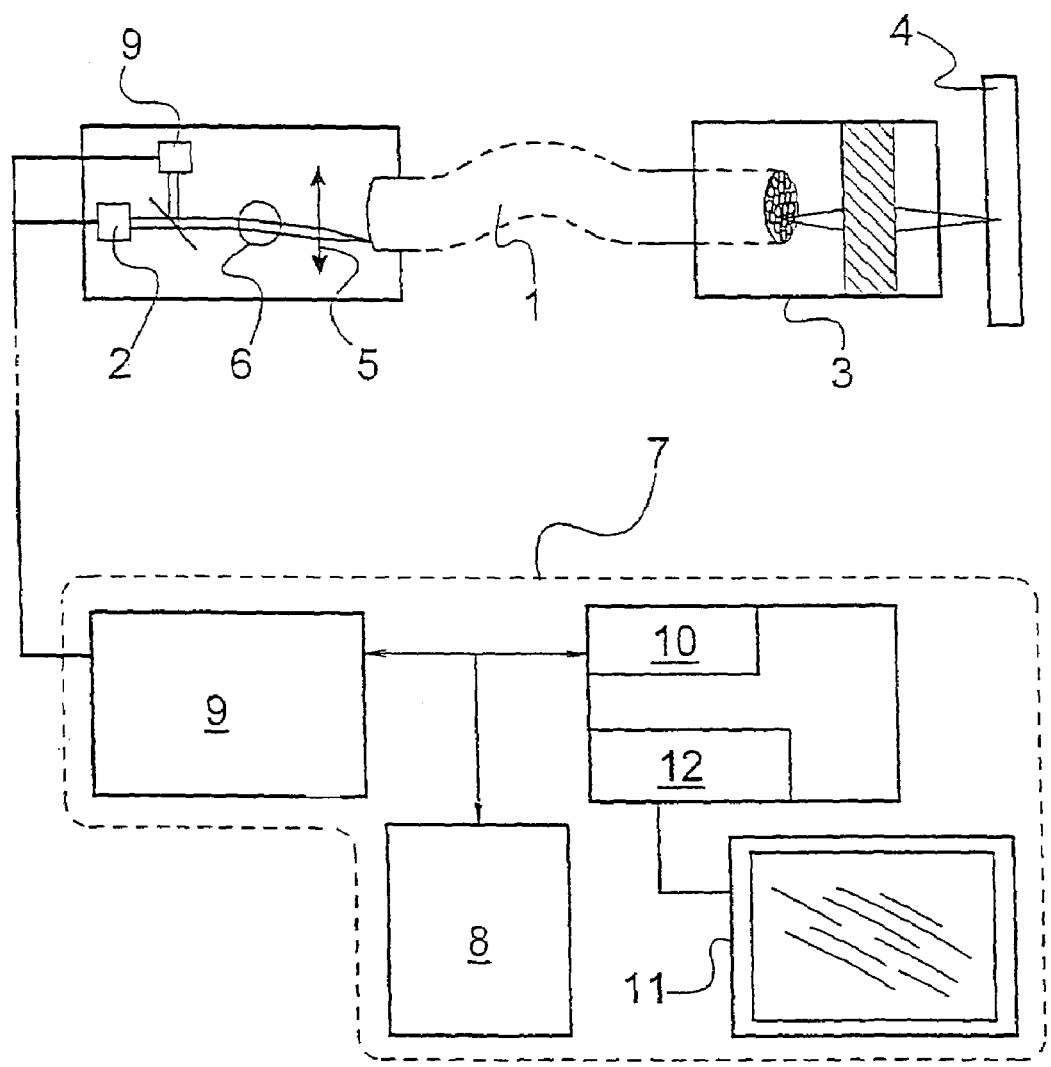
FIG. 1 is a general diagram of an example of a fibre confocal imaging system implementing the method according to the invention.

FIG. 1 shows a coherent bundle of flexible optical fibres forming an image guide 1 with, on its proximal end, a light source 2 and a fibre injection system allowing the fibres to be illuminated one by one and, on its distal end, an optical head 3 allowing the beam leaving the illuminated fibre to be focussed at a point situated at a given depth in the observed object 4. The injection system comprises several optical elements 5 preceded by a fibre scanning system 6, such as a deflection unit, allowing the fibres to be scanned one by one at very high speed. Each fibre is used in turn to carry the light beam and also the corresponding return beam originating from the observed object. The spatial resolution is obtained by focussing the laser beam into a point and by the confocal character inherent in the spatial filtering of the object observed by the same fibres as those which served for the illumination. This makes it possible to receive, using a photodetector 9, exclusively the signal originating from the observed object and to produce an image point by point.

The image guide 1 is constituted by a very large number of flexible optical fibres, for example 30,000 fibres 2 μm in diameter and spaced 3.3 μm apart. In practice, it is possible to use either all of the fibres of the image guide, or a chosen sub-group of these fibres, for example centred.

The electronic and computer means 7 for control, analysis and digital processing of the signal detected and for display in particular include the following cards:
  a synchronization card 8 the functions of which are:
  for controlling the scanning in a synchronized manner;
  for knowing at any moment in time the position of the laser spot thus scanned; and
  for managing all the other cards by means of a microcontroller which can itself be controlled;
  a detector card 9 which comprises an analogue circuit which in particular carries out an impedance matching, an analogue-to-digital converter then a programmable logic component (for example an FPGA circuit) which shapes the signal;
  a digital acquisition card 10 which allows processing of a digital data stream with variable frequency and its display on a screen 11;
  a graphics card 12.

As a variant, a single card combining the functionalities of these different cards can be used.

These electronic and computer means 7, which are able to carry out the steps of the method according to the invention, can be presented in the form of a microcomputer equipped with processing means necessary for calculating the velocity of the red blood cells.

Figure 2:
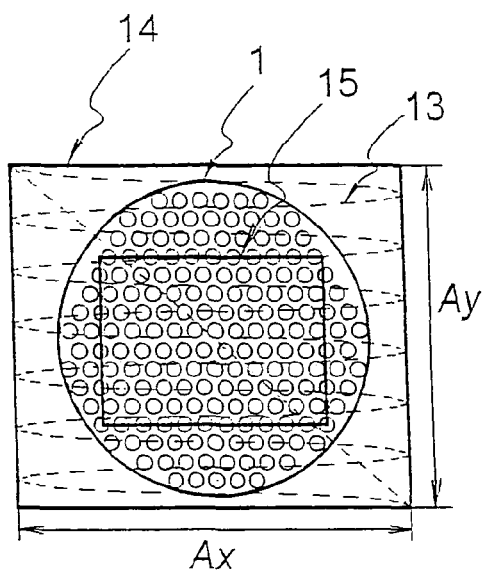
FIG. 2 is a very simplified diagram illustrating the scanning method of the imaging system of FIG. 1.

FIG. 2 is a very simplified diagram illustrating the scanning method of the imaging system of FIG. 1. The scanning laser spot is symbolized by the dotted lines 13 which describe a conventional scanning trajectory in a square scanning window 14. The trajectory of the laser spot 13 is a "Z" from top to bottom. The horizontal velocity $V_x$ along the horizontal axis $A_x$ is assumed to be very high compared to the velocity $V_y$ along the axis $A_y$. This hypothesis involves ignoring the time the spot takes to catch up with the blood cell between two horizontal scans. It is also a combination of the effect observed on the even lines with that observed on the odd lines. By way of example, the velocity $V_y$ can be 3 mm/s, while that of $V_x$ can be 5 m/s.

Figure 3:
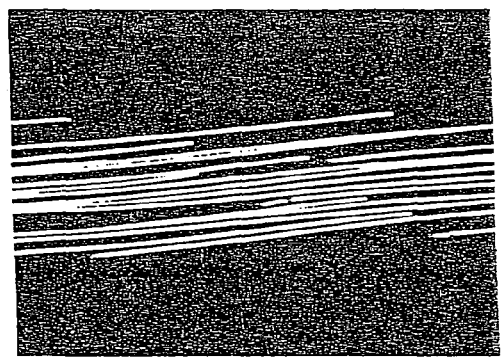
FIG. 3 is a diagrammatic image representing ridges, this image originating from a simultaneous acquisition.

In FIG. 2, inside the scanning window 14, the image guide 1 is also represented according to a transverse cross-sectional view. The optical fibres are represented in the form of coherent circles. The imaged zone 15 only corresponds to a limited number of optical fibres situated inside a rectangle. The laser beam is successively injected into each of the optical fibres. The image represented in FIG. 3, simulates an acquisition, i.e. each fibre has been injected only once. This image shows oblique ridges corresponding to the interaction between the scanning system and the moving particles.

The appearance of these ridges is explained by the interaction between the image of the red blood cells and the image formation mechanism. The laser spot carries out the scanning according to a Z-shaped trajectory, a measurement is carried out at a set of positions of the laser, for example 896 measurements per line over 640 lines. A moving red blood cell will be intersected at a given position on one line of the scan. On the following line, this blood cell is still intersected, however it has moved relative to the preceding line. This phenomenon continues as long as the intersection between the scanning line and the blood cell exists. This phenomenon then creates a ridge the slope of which is a function of the velocity of the red blood cell.

Figure 4:
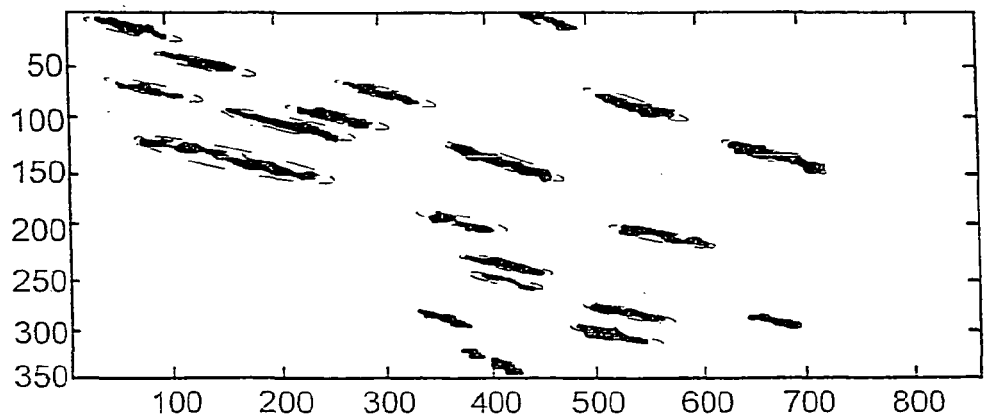
FIG. 4 is a diagrammatic view of a step of selecting ridges.

In FIG. 4, after acquisition of an image, the ridges are shown. A thresholding makes it possible to retain only the most significant ridges. Each ridge is then framed by an ellipse allowing a slope to be defined. Then, the electronic and computer means 7 determine the slope of each ridge so as to calculate the velocity of each red blood cell.

This invention therefore makes it possible to determine the velocity from a single image. This makes it possible in particular to avoid problems of blurring during coordination of images. It advantageously allows high velocities to be picked up opposite the field of view and the frequency of acquisition. By way of example, an 11 Hz image acquisition system makes it possible to pick up velocities of the order of 5 to 25 mm/sec, i.e. velocities which are impossible to estimate with most of the techniques of the prior art.

Preferably, the velocity of the blood cell, the vertical movement of which does not reach the spot, is measured. Generally, the angle of the trajectory must be situated between the horizontal and the critical angle at which the vertical velocity of the blood cell becomes equal to that of the spot.

Of course, the invention is not limited to the examples which have just been described and numerous adjustments can be made to these examples without exceeding the scope of the invention. In particular, measurements carried out on several ridges, or on several images can be envisaged in order to improve precision.

The invention claimed is:

1. Method for measuring the velocity of a microscopic object moving inside a flow, using a light-scanning microscope, this method comprising the following steps:
  acquisition of an image by x and y light scanning of a plane containing said object;
  detection in the plane (x, y) of a ridge produced by the movement of said object during the acquisition of said image;
  determination of the slope of said ridge in the plane (x, y); and
  estimation of the velocity $V_g$ of said object from the thus-determined slope.

2. Method according to claim 1, characterized in that the step of detection of the ridge comprises the following steps:
  enhancement of a group of ridges of the image by application of a filter;
  application of a threshold in order to retain the most significant ridges;
  fitting a straight line or an ellipse on each of these ridges; and
  identification of said ridge.

3. Method according to claim 1, characterized in that the velocity $V_g$ of said object is given by the following equation: $V_g * \cos(\theta) = V_y / \tan(\alpha)$ with $V_y$ being the vertical velocity of the light spot used for the scanning, and "α" the angle between the horizontal axis "x" and the ridge.

4. Method according to claim 3, characterized in that the angle θ is obtained by detection of the edges of the blood vessels conveying the object.

5. Method according to claim 3, characterized in that, in order to obtain the angle θ, said object is assimilated to a vertical rod with a finished height D and the angle θ is calculated from the following equation:

$$L = \frac{D}{|V_y - V_g \sin\theta|} \sqrt{V_y^2 + V_g^2 \cos^2\theta}$$

where L is the length of the ridge.

6. Method according to claim 5, characterized in that in the case where $V_g*\sin(\theta)<V_y$:

$$\tan\theta = \tan\alpha - \frac{D}{L\cos\alpha}$$

$$V_g = |V_y|\sqrt{\left(1-\frac{D}{L\sin\alpha}\right)^2 + \frac{1}{\tan^2\alpha}}.$$

7. Method according to claim 5, characterized in that in the case where $V_g*\sin(\theta)>V_y$:

$$\tan\theta = \tan\alpha + \frac{D}{L\cos\alpha}$$

$$V_g = |V_y|\sqrt{\left(1+\frac{D}{L\sin\alpha}\right)^2 + \frac{1}{\tan^2\alpha}}.$$

8. Method according to claim 5, characterized in that a second image is acquired of the same plane but in a reversed scanning, and the following equation is used:

$$L' = \frac{D}{|-V_y - V_g\sin\theta|}\sqrt{V_y^2 + V_g^2\cos^2\theta}$$

where L' is the length of the ridge during the reversed scanning.

9. Method according to claim 8, characterized in that when $|V_g*\sin\theta|<|V_y|$:

$$\tan\theta = \tan\alpha\frac{L-L'}{L+L'}$$

$$V_g = |V_y|\sqrt{\left(\frac{L-L'}{L+L'}\right)^2 + \frac{1}{\tan^2\alpha}}$$

where L is the length of the ridge in a first direction of scanning, and L' the length of the ridge during the reversed scanning.

10. Method according to claim 8, characterized in that when $|V_g*\sin(\theta)|>|V_y|$:

$$\tan\theta = \tan\alpha\frac{L+L'}{L-L'}$$

$$V_g = |V_y|\sqrt{\left(\frac{L+L'}{L-L'}\right)^2 + \frac{1}{\tan^2\alpha}}.$$

11. Method according to claim 3, characterized in that when $V_g*\sin(\theta)=V_y$, in order to determine $V_g$ and $\theta$ the following equation is also used:

$$V_g = \left|\frac{V_y}{\sin\alpha}\right|.$$

12. Method according to claim 3, characterized in that as said object is a red blood cell, its form on the acquired image is assimilated to an ellipse with a radius R the angle α of which between the ridge and the "x" axis is given by:

$$\tan(2\alpha) = \frac{2\cos(\theta)}{\frac{V_g}{V_y} - 2\sin(\theta)}$$

and the length of the principal axis is given by:

$$L = \frac{2R\sqrt{2}}{\sqrt{V_r^2 - 2V_r\sin(\theta) + 2 - |V_r|\sqrt{V_r^2 - 4V_r\sin(\theta) + 4}}}$$

with $V_r = \frac{V_g}{V_y}$.

13. Method according to claim 1, characterized in that a confocal microscope is used.

14. Method according to claim 1, characterized in that a light-scanning microscope in fibre mode is used.

15. Method according to claim 1, characterized in that a non-fibre light-scanning microscope is used.

16. Light-scanning microscopy system, used to measure the velocity of a microscopic object moving inside a flow, this system implementing a method according to any one of the preceding claims; this system comprising:
 means for acquiring an image by x and y light scanning of a plane containing said object;
 means for detecting in the plane (x, y) a ridge produced by the movement of said object during the acquisition of said image;
 means for determining in the plane (x, y) the slope of said ridge; and
 means for estimating the velocity $V_g$ of said object from the thus-determined slope.

17. System according to claim 16, characterized in that during detection of the ridge, the system comprises:
 means for enhancing a group of ridges of the image by application of a filter;
 means for applying a threshold so as to retain the most significant ridges;
 means for fitting an ellipse on each of these ridges; and
 means for identifying said ridge.

18. System according to claims 16, characterized in that a confocal microscope is used.

19. System according to claim 16, characterized in that a light-scanning microscope in fibre mode is used.

20. System according to claim 16, characterized in that a non-fibre light-scanning microscope is used.

21. Method according to claim 3, characterized in that a second image is acquired of the same plane but in a reversed scanning, and the following equation is used:

$$L' = \frac{D}{|-V_y - V_g\sin\theta|}\sqrt{V_y^2 + V_g^2\cos^2\theta}$$

where L' is the length of the ridge during the reversed scanning.

* * * * *